(12) United States Patent
Moore

(10) Patent No.: US 7,939,803 B2
(45) Date of Patent: May 10, 2011

(54) METHOD AND APPARATUS FOR DETECTING EXPLOSIVES

(75) Inventor: David Steven Moore, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 273 days.

(21) Appl. No.: 11/877,775

(22) Filed: Oct. 24, 2007

(65) Prior Publication Data

US 2009/0107758 A1    Apr. 30, 2009

(51) Int. Cl.
*G01N 33/22* (2006.01)
(52) U.S. Cl. .................................................. 250/338.1
(58) Field of Classification Search ............... 250/338.1
See application file for complete search history.

(56) References Cited

U.S. PATENT DOCUMENTS

| | | | |
|---|---|---|---|
| 5,227,800 A * | 7/1993 | Huguenin et al. | 342/179 |
| 6,026,135 A * | 2/2000 | McFee et al. | 376/159 |
| 6,216,540 B1 * | 4/2001 | Nelson et al. | 73/633 |
| 6,343,534 B1 * | 2/2002 | Khanna et al. | 89/1.13 |
| 6,786,098 B2 * | 9/2004 | Bates | 73/606 |
| 2002/0121602 A1 * | 9/2002 | Thomas et al. | 250/341.6 |
| 2002/0175849 A1 * | 11/2002 | Arndt et al. | 342/22 |
| 2004/0114130 A1 * | 6/2004 | Nguyen et al. | 356/36 |
| 2005/0167596 A1 * | 8/2005 | Rothenfusser et al. | 250/341.6 |
| 2007/0045544 A1 * | 3/2007 | Favro et al. | 250/341.6 |
| 2007/0075246 A1 * | 4/2007 | Gatt | 250/341.6 |
| 2007/0118324 A1 * | 5/2007 | Gulati | 702/131 |
| 2008/0246619 A1 * | 10/2008 | Colson et al. | 340/584 |

* cited by examiner

*Primary Examiner* — David P Porta
*Assistant Examiner* — Djura Malevic
(74) *Attorney, Agent, or Firm* — Husch Blackwell LLP

(57) ABSTRACT

A method and apparatus is provided for detecting explosives by thermal imaging. The explosive material is subjected to a high energy wave which can be either a sound wave or an electromagnetic wave which will initiate a chemical reaction in the explosive material which chemical reaction will produce heat. The heat is then sensed by a thermal imaging device which will provide a signal to a computing device which will alert a user of the apparatus to the possibility of an explosive device being present.

21 Claims, 1 Drawing Sheet

METHOD AND APPARATUS FOR DETECTING EXPLOSIVES

STATEMENT REGARDING FEDERAL RIGHTS

This invention was made with government support under contract number DE-AC52-O6NA25396 awarded by the U.S. Department of Energy. The government has certain rights in the invention.

BACKGROUND OF INVENTION

The use of explosive devices has unfortunately become commonplace in theaters of conflict. Many attacks are made on soldiers using IED's (improvised explosive devices). These weapons can be used effectively at times. While countermeasures are sometimes available, they have so far proved to not be as effective as desired particularly when convoys are moving down roads at practical speeds. IED's can be triggered by proximity devices or may be triggered remotely through the use of a signal transmitter like a cell phone. Vehicles are being designed to withstand such explosions but even they may not be effective if the explosive device is large. Additionally, explosive devices may also be effectively utilized by people as so called suicide bombers.

Explosive devices typically contain an explosive that is detonated through a chemical reaction that produces heat. In order to detonate such an explosive device, the heat which may be provided by a shock or impact, a detonator, or generated in situ by initiating the chemical reaction with enough energy that the reaction is self sustaining.

It would be desirable to provide a means for detecting an explosive device which will not detonate the device and which means can be used to quickly detect such explosive devices while moving at a substantial speed. The detection means should be capable of detecting the explosive device far enough in advance, both time wise and distance wise, to provide sufficient warning to avoid danger.

IED's are presently detected at stand-off distances using magnetics, radio frequencies, and visual clues, none of which are specific to explosives containing objects. Closer proximity detection includes explosive detectors which are not amenable to stand-off detection at convoy speeds. Air-coupled ultrasonics are being used to measure density gradients in test explosives. Thermal imaging is being used to detect personnel and chemical releases but is plagued by fluctuating background thermal clutter.

Thus, there is a need for an improved explosives detection apparatus and method.

SUMMARY OF INVENTION

The present invention involves the provision of a method of detecting explosive devices using waveform energy at a frequency adequate to cause explosive material to increase in temperature. The method includes scanning a suspect area including any present explosive device to sense an increase in the temperature of the explosive material. A detection system is provided to sense the temperature difference between extraneous background and foreground materials and the explosive material thereby indicating the possible existence of explosive material and thereafter initiating countermeasures.

The present invention also involves the provision of an apparatus usable to detect explosive devices at an adequate stand-off distance that can be usable in a moving convoy or the like. The device includes a wave transmitter operable for transmitting an energy carrying wave for a first period of time. The wave transmitter is tuned to cause an explosive material to selectively heat. A receiver is provided and is operable to receive thermal data from an area where the wave was projected. The receiver provides an output signal indicative of a thermal image. A computing device is operably coupled to the receiver to process the thermal imaging data from the receiver and provide an output signal indicative of a thermal image of a scanned area to indicate an increase in temperature after the area has been exposed to the transmitted wave. The computing device can provide a visual output for an operator and/or may be programmed to initiate an alarm automatically after which a person can respond or view a thermal image to determine the location of the explosive device.

BRIEF DESCRIPTION OF DRAWINGS

Like numbers throughout the various figures designate like or similar parts and/or construction.

DETAILED DESCRIPTION

Figure 1:
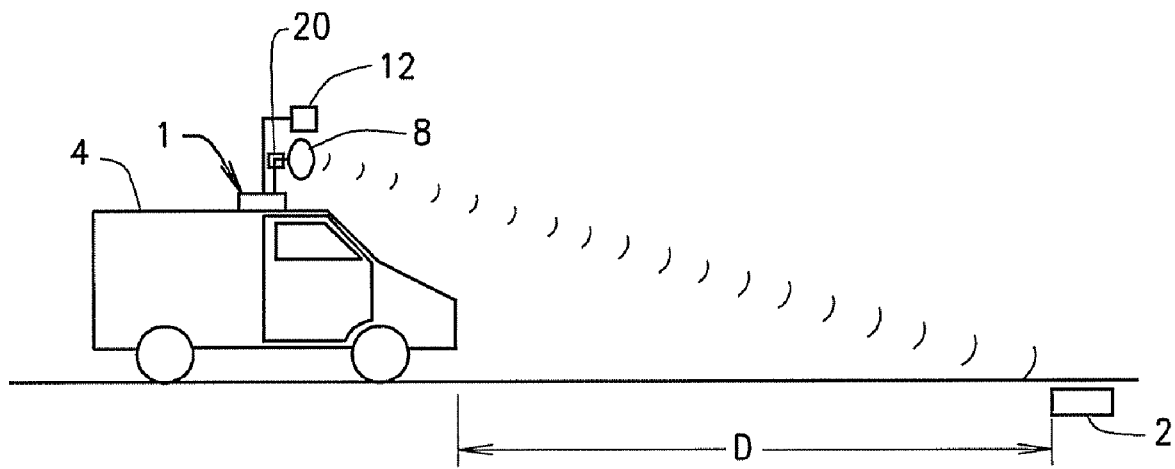
FIG. 1 is a schematic illustration of a mobile device carrying a wave transmitter.
Figure 2:
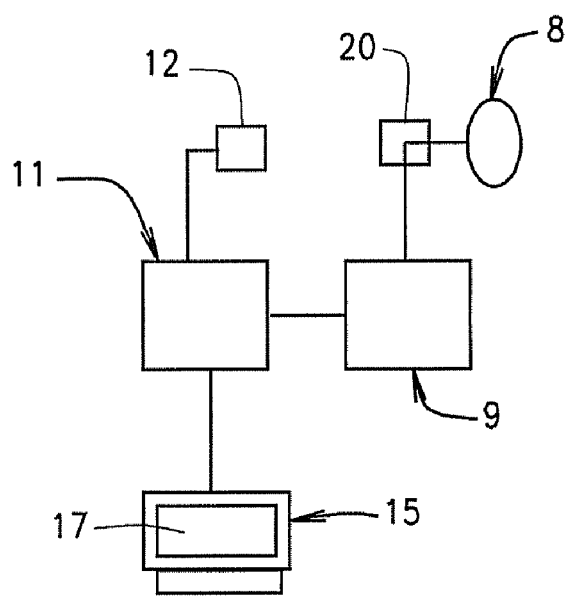
FIG. 2 is a block diagram of an apparatus adapted for detecting explosive devices.

The reference numeral 1 designates generally an apparatus usable to detect the possible presence of an explosive device 2 at a stand-off distance D. The apparatus 1 may be carried by a motorized vehicle 4 if desired to provide a mobile energy source. The explosive device 2 may be a formed quantity of explosive material which may be encased or not encased in a housing such as a projectile carrying an explosive charge. The apparatus 1 includes a wave transmitter 8 operable to transmit a wave carrying energy such as an ultrasonic wave and that is capable of columnating the waves so that they can be focused to increase the energy density at the target area of interest. The transmitter 8 is connected to a wave generator 9 (FIG. 2) that will generate the appropriate wave and wave frequency. The generator 9 is preferably an ultrasonic generator having an operating frequency range in the range of between about 50 kHz and about 1 MHz. The wave generator is operable to provide for an adjustment of the frequency to tune the output waves to a particular frequency for one or more explosive materials and to adjust the amplitude of the waves to obtain the desired energy being transmitted. It is to be understood though that the generator may have a fixed output for both amplitude and frequency whereby the generator 9 can be optimized for a particular type of explosive. By having a variable output, an operator may be able to tune the wave output to search for different types of explosives that may respond differently to the incident waveform. A thermal imaging receiver 11 is provided and is operable to scan or view the area on which the waves were transmitted and view a thermal image of the area of interest both before and after exposure to the wave energy. The receiver 11 includes a sensor 12 operable to view an area for a thermal image and preferably provide a sensitivity of about 0.05° C. or lower.

Explosive material generates an explosion by release of chemical energy from the explosive material once sufficient energy is imparted into the explosive compound to effect detonation. It has been found that this chemical reaction can be initiated and generate heat but not to such a degree to effect detonation. The wave energy is converted to thermal energy by a chemical reaction in the explosive material. This then can be sensed by the sensor 12 to provide an output signal from the receiver 11 to the computing device 15.

The receiver 11 provides an output signal to the computing device 15. The computing device 15 is operable to process the signal from the receiver 11 and in turn provide an output signal in response to the signal processing. The computing device 15 can be any suitable device, for example, a standard PC laptop. The computing device 15 can provide an output signal in various forms, for example, a warning such as an audible or visual warning, for example, a sound, a flashing light or the like. This warning is operable to alert an operator to view a more detailed output signal, for example, a thermal image on a screen 17 so the operator can determine whether or not there is a possibility of an explosive device within the scanned area and the potential location of the explosive device 2. In order to effect sweeping of an area of interest, the transmitter 8 may be mounted on an azimuth/elevation sweep mount 20. The mount 20 is preferably power operated and its movement may be automated, manual or both. The receiver 12 may be similarly mounted and its movement coordinated with that of the transmitter 8 or may track the movement out of time phase to allow time for the explosive material to increase in temperature. Such time lag phase of a few seconds, e.g., on the order of 1 to 5 seconds provides time for the increase in explosive temperature to occur and transfer to a viewable surface. Additionally, the sensor 12 may have a broader scope of coverage than the transmitter 8.

A suitable transmitter 8 is preferably an air coupled aimable ultrasonic driver 9 capable of changing the output frequency and having a power output on the order of about 1 kW or more. The output frequency is preferably in the range of about 50 kHz to about 1 MHz. The focusing of the output can be done by using a phased ultrasonic transducer array or a spherical transducer array. Suitable transducers include AIRSCAN transducers made by QMI, Inc. of Huntington Beach, Calif. Such focusing of the sound wave and an azimuth/elevation aimable mount are well known in the art.

The sensor 12 can be a thermal imaging camera, for example, an Image IR made by Santa Barbara Focalplane of Santa Barbara, Calif. capable of 50 mK or lower temperature resolution and preferably about 20 mK or lower temperature resolution and have a frame rate of greater than about 30 Hz. The signal received by the computing device 15 may be processed by software, for example, Igor software available from WaveMetrics of Lake Oswego, Oreg. to indicate a change in temperature in the area sensed after the area has been exposed to wave energy. The wave form energy would have a preselected angle of divergence of preferably less than about 10° total included angle. This allows the apparatus 1 to be used at a substantial standoff range of at least about 50 meters to provide an appropriate stand-off distance D and provide sufficient warning that there is a possible explosive device in the area. A suitable standoff distance D is in the range of between about 50 meters and about 100 meters. Such an angle of divergence allows for a lower energy output and higher resolution of objects within the area of interest.

In a preferred embodiment, the wave energy is transmitted for a preselected period and at a preselected frequency depending upon the particular type of explosive being sought. In one example, the waves may be transmitted for approximately one second and then the transmitter turned off or redirected, if desired, while the thermal imaging system including the receiver 11 and sensor 12 scan the area exposed to the wave seeking out an increase in temperature from a prior thermal image scan or from an early portion of the current thermal image scan. The receiver 11 and computing device 15 look not only for an increase in temperature but for the phase of the response which phase can be programmed into the computing device 15 to assist in separating thermal clutter from a potential explosive device. The system 1 may be tuned for a particular explosive or series of explosives and can discriminate between explosives and non-explosives by looking for the phase of response and the temperature of the response. In one embodiment, the system would look for an approximate 1° C. increase in temperature after exposure of the explosives to the energy in the wave.

The above-described system utilizes an output wave of sound in the ultrasonic range, for example 50 kHz to 1 MHz with the frequency being selected for a particular type of explosive or types of explosives. It has also been found, that the sound waves may be generated in the explosive device by exposing the explosive device to electromagnetic waves in the microwave range. In a preferred embodiment, the electromagnetic waves are preferably sent simultaneously at two separate frequencies which can cause objects to generate sound waves at a beat frequency generally equal to the difference between the two separate electromagnetic frequencies in situ in the explosive device which can then activate the chemical reaction in the explosive to create the increase in temperature which can then be sensed by the sensor 12. The difference in the two electromagnetic frequencies is in the range of between about 50 kHz and about 1 MHz. The output energy of such an electromagnetic wave or waves at different frequencies is on the order of at least about 1 kW and would have an angle of divergance of less than about 10° total included angle.

Ultrasonic energy, in the sound wave form of the invention, is transmitted in a desired direction, which is scannable through a variety of azimuths and elevations. The ultrasonic energy may be pulsed on and off at a given rate selected for known explosives responses. A thermal imaging camera is aimed in the same direction, and observes the screen components excited by the ultrasonic transmitter. The thermal imaging camera obtains signal average images and bins them according to whether the ultrasonic excitation is present or absent. The binning process includes a phase delay that accounts for the rate at which ultrasonic energy produces the desired enhanced thermal signal in the target. The ultrasonic energy is transmitted through any container wall (i.e., metal, plastic, wood, or other material) of a explosive device located in the excitation field of view and excites the explosive material acoustic resonances. These resonances localize the acoustic energy and produce a region of higher temperature (the hot spot) at which the explosive begins to react. The reaction then stops after the wave energy is turned off or redirected because the hot spot is either too small or too cool to propagate, but leaves behind a thermal wave that is transmitted to the explosive device surface, where it is observed by the thermal imager. Inert materials do not contain the stored chemical energy of explosives so their temperature rises much slower. The chemical energy release at the hot spot in the explosive causes an enhanced thermal signal that is unique to explosives.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

The invention claimed is:

1. A method of detecting explosive devices comprising:
exposing an area potentially containing an explosive material in an explosive device to sound waves at a frequency adequate to cause the explosive material to increase in temperature due to a chemical reaction initiated in the explosive material;
scanning the area to sense an increase in temperature;
providing a signal indicative of a thermal state of the area after at least a portion of the exposing; and
determining whether the detected increase in temperature is sufficient to be caused by the chemical reaction in the explosive material.

2. The method of claim 1 wherein the sound waves being projected from a source at a substantial distance from the explosive device.

3. The method of claim 1 wherein the energy source creating the sound waves being used is moving during said exposing.

4. The method of claim 1 wherein the sound waves being generated directly by a mobile energy source and the sound waves being emitted at a frequency in the range of between about 50 kHz and about 1 MHz.

5. The method of claim 1 wherein the sound waves being generated in the explosive device by a mobile energy source adapted to project microwave energy operable to create sound waves in an explosive device to cause the explosive material to heat.

6. The method of claim 5 wherein the microwave energy being emitted at at least two frequencies with a difference in the two frequencies being in the range of between about 50 kHz and about 1 MHz.

7. The method of claim 4 wherein the time of emitting sound waves being selected to increase the temperature of the explosive material by at least about 1° C.

8. The method of claim 7 wherein the sound waves being emitted intermittently.

9. The method of claim 7 wherein the sound waves being emitted for a first period of time followed by a temperature scan for a second period of time.

10. The method of claim 1 wherein the sound waves being tuned in amplitude, frequency and time period of intermittent emission for a selected type of explosive material.

11. The method of claim 1 including using a computing device and analyzing the received signal indicative of a thermal state of the area and determining if there is a potential explosive device in the scanned area and providing an alert if one is possibly sensed.

12. The method of claim 11 including focusing the emitted sound waves at a preselected angle of divergence.

13. An explosive material location device comprising:
a wave transmitter operable for transmitting an energy carrying wave for a first period of time, the wave transmitter generating a frequency adequate to cause an explosive material to increase in temperature due to a chemical reaction initiated in the explosive material;
a receiver operable to receive thermal data from an area where the wave was projected to and to provide an output signal; and
a computing device operably coupled to the receiver to process data from the receiver and provide an output signal indicative of a thermal image of a scanned area to indicate an increase in temperature after the area has been exposed to the wave, the computing device being configured to determine whether the detected increase in temperature is sufficient to be caused by the chemical reaction in the explosive material.

14. The device of claim 13 wherein the wave transmitter including an ultrasonic generator coupled to a sound output device having an output sound wave at a frequency in the range of between about 50 kHz and about 1 MHz.

15. The device of claim 14 wherein the output sound wave has a magnitude of at least about 1 kW.

16. The device of claim 13 wherein the wave transmitter including an electromagnetic wave generator system coupled to an output device having an electromagnetic wave output capable of causing an explosive device to vibrate at a frequency in the range of between about 50 kHz and about 1 MHz.

17. The device of claim 16 wherein the electromagnetic wave output is in the microwave range.

18. The device of claim 17 wherein the electromagnetic wave output device being operable to output at least two different frequencies simultaneously.

19. The device of claim 13 wherein the frequency is optimized to cause a particular type of explosive material to increase in temperature.

20. The method of claim 1 wherein the frequency is optimized to cause a particular type of explosive material to increase in temperature.

21. The method of claim 1 further comprising providing a visual output of the exposed area to seek an increase in temperature to indicate the possible existence of explosive material in the target area.

\* \* \* \* \*